US012144671B2

(12) United States Patent
Stamm et al.

(10) Patent No.: US 12,144,671 B2
(45) Date of Patent: Nov. 19, 2024

(54) UNIVERSAL PHANTOM FOR CALIBRATION AND VERIFICATION OF OPTICAL AND RADIATION SYSTEMS

(71) Applicant: Varian Medical Systems International AG, Steinhausen (CH)

(72) Inventors: Christian Stamm, Baden (CH); Stefan Scheib, Waedenswil (CH); Andrea Kisrákói, Dunakeszi (HU); Roland Meier, Herzogenbuchsee (CH)

(73) Assignee: Siemens Healthineers International AG, Steinhausen (CH)

( * ) Notice: Subject to any disclaimer, the term of this patent is extended or adjusted under 35 U.S.C. 154(b) by 119 days.

(21) Appl. No.: 17/560,005

(22) Filed: Dec. 22, 2021

(65) Prior Publication Data

US 2023/0190221 A1 Jun. 22, 2023

(51) Int. Cl.
| A61B 6/00 | (2024.01) |
| A61B 6/58 | (2024.01) |
| A61B 90/00 | (2016.01) |
| A61N 5/10 | (2006.01) |

(52) U.S. Cl.
CPC ............. *A61B 6/583* (2013.01); *A61B 90/39* (2016.02); *A61N 5/1075* (2013.01); *A61B 2090/3937* (2016.02); *A61N 2005/1076* (2013.01); *A61N 2005/1087* (2013.01); *A61N 2005/1089* (2013.01); *A61N 2005/1091* (2013.01)

(58) Field of Classification Search
None
See application file for complete search history.

(56) References Cited

U.S. PATENT DOCUMENTS

| 5,923,727 | A | 7/1999 | Navab | |
| 6,493,574 | B1* | 12/2002 | Ehnholm | A61B 5/055 |
| | | | | 378/207 |
| 7,844,094 | B2 | 11/2010 | Jeung et al. | |
| 9,962,561 | B2 | 5/2018 | Meir et al. | |
| 10,456,601 | B2 | 10/2019 | Meir et al. | |
| 10,933,258 | B2 | 3/2021 | Meir et al. | |
| 2008/0167550 | A1* | 7/2008 | Weiser | A61B 6/4441 |
| | | | | 348/E5.086 |
| 2010/0046718 | A1* | 2/2010 | Weiser | G06T 7/73 |
| | | | | 378/163 |
| 2011/0004431 | A1* | 1/2011 | Ringholz | A61B 6/4441 |
| | | | | 702/94 |

(Continued)

FOREIGN PATENT DOCUMENTS

| EP | 3501397 A1 | 6/2019 |
| GB | 2516282 A | 1/2015 |

(Continued)

*Primary Examiner* — Hoon K Song
(74) *Attorney, Agent, or Firm* — Harness, Dickey & Pierce, P.L.C.

(57) ABSTRACT

A universal phantom includes a first phantom and a second phantom. The first phantom comprises a plurality of radiation markers. The second phantom comprises a plurality of optical markers. The second phantom is fixedly attachable to the first phantom in a predetermined position. A calibration method employs a universal phantom to consolidate the tasks of determining the isocenter of a radiation machine, calibrating optical devices, and registering the optical devices in a radiation coordinate system with origin at the isocenter.

21 Claims, 12 Drawing Sheets

(56) References Cited

U.S. PATENT DOCUMENTS

| | | |
|---|---|---|
| 2016/0089106 A1 | 3/2016 | Kirby et al. |
| 2017/0219498 A1 | 8/2017 | Chtcheprov et al. |
| 2018/0339173 A1 | 11/2018 | Kilby et al. |
| 2019/0192105 A1 | 6/2019 | Mewes et al. |
| 2019/0350685 A1* | 11/2019 | Saghatchi ............ A61C 8/0089 |

FOREIGN PATENT DOCUMENTS

| | | |
|---|---|---|
| WO | WO 2014165611 A1 | 10/2014 |
| WO | WO 2018217763 A1 | 11/2018 |

* cited by examiner

UNIVERSAL PHANTOM FOR CALIBRATION AND VERIFICATION OF OPTICAL AND RADIATION SYSTEMS

TECHNICAL FIELD

This application relates generally to radiation treatment and imaging. In particular, various embodiments of a phantom device and a method of calibration and verification of optical and radiation systems are described.

BACKGROUND

Optical devices such as stereoscopic (3D) cameras, 2D cameras, time-of-flight (ToF) cameras, LiDAR, or structured light cameras are often used in radiation systems to aid patient setup, verify patient identification, monitor treatment, or provide guidance such as in surface guided radiotherapy (SGRT). The use of optical devices in a radiation system requires calibration of the optical devices in the radiation coordinate system.

Conventionally, calibration of optical devices in a radiation coordinate system requires a multitude of calibration tools to perform various calibration steps to ensure that the optical devices are calibrated, aligned to each other, and registered to the radiation coordinate system. For instance, to calibrate stereoscopic cameras in a treatment or diagnostic coordinate system, conventional techniques use a calibration sheet to calibrate the stereo cameras, and a separate, x-ray detectable three-dimensional (3D) object to register the stereo cameras to the treatment or diagnostic coordinate system. To register the cameras to the radiation coordinate system, a sophisticated computer model of the 3D object is needed in combination with a geometrically accurate phantom, or geometrical matching of a treatment plan (in case of treatment application) is based on a CT scan, where the x-ray image to align typically shows a slightly smaller 3D object than what the stereo cameras view. The latter is caused by the edge artifacts, which do not allow sharp detection of the object outline. Conventional calibration tools are expensive. The entire calibration and registration process is labor-intensive and provides limited accuracy.

Therefore, there is a need for solving the problems or limitations of conventional calibration techniques. It would be desirable to provide a universal phantom consolidating several tools into one solution, allowing calibration and registration of optical devices in a radiation coordinate system more effectively and efficiently.

SUMMARY

In one aspect, embodiments of the disclosure feature a universal phantom or an apparatus useful in calibration of an optical and/or radiation system. In general, an embodiment of the apparatus comprises a first phantom and a second phantom. The first phantom comprises a plurality of radiation markers. The second phantom comprises a plurality of optical markers. The second phantom is fixedly attachable to the first phantom in a predetermined position.

In various embodiments of the aspect, the first phantom comprises a three-dimensional (3D) body, and the plurality of radiation markers are distributed in the 3D body.

In various embodiments of the aspect, the second phantom comprises a board member having a planar surface, and the plurality of optical markers are arranged in a two-dimensional (2D) pattern in the planar surface.

In various embodiments of the aspect, the second phantom further comprises one or more radiation markers.

In various embodiments of the aspect, the board member of the second phantom is generally radiation-transparent.

In various embodiments of the aspect, the second phantom comprises a modular unit, allowing the second phantom to be fixedly attached to the first phantom in a first orientation and a second orientation different from the first orientation.

In various embodiments of the aspect, the first phantom comprises a three-dimensional (3D) body, and the plurality of radiation markers are distributed in the 3D body. The second phantom comprises a board member having a planar surface, and the plurality of optical markers are arranged in a two-dimensional (2D) pattern in the planar surface. The board member of the second phantom is fixedly attachable to the 3D body of the first phantom in a first orientation and a second orientation different from the first orientation. In a specific embodiment, the 3D body of the first phantom is generally in the form of a cylinder, partial cylinder, or cube, the board member of the second phantom has a cut-out, and at least a portion of the 3D body of the first phantom is disposed in the cut-out of the board member. In a specific embodiment, the second phantom further comprises a plurality of radiation markers.

In various embodiments of the aspect, the apparatus further comprises a radiation machine operable at a megavoltage energy level and comprising a first source configured to produce radiation suitable for treatment of a patient. In a specific embodiment, the radiation machine further comprises a second source operable at a kilovoltage energy level to produce radiation suitable for imaging an object. In a further specific embodiment, the apparatus further comprises one or more optical devices.

In various embodiments of the aspect, the apparatus comprises a source of radiation operable to produce x-rays, protons, heavy ions, electrons, and any other types of radiation.

In another aspect, embodiments of the disclosure feature a method of calibrating a system comprising a radiation machine and one or more cameras. In general, an embodiment of the method comprises the steps of positioning a phantom device at or approximately at an isocenter of the radiation machine, wherein the phantom device comprises a first phantom comprising a plurality of radiation markers and a second phantom comprising a plurality of optical markers, and the second phantom is fixedly attached to the first phantom in a predetermined position; acquiring images containing the radiation markers of the first phantom with radiation from the radiation machine; determining the isocenter of the radiation machine using the images containing the radiation markers of the first phantom; defining a position of the first phantom in a first coordinate system with origin at the isocenter, and defining a position of the second phantom in the first coordinate system based on the predetermined position of the second phantom relative to the first phantom; calibrating the one or more cameras in a second coordinate system relative to the second phantom using images containing the optical markers of the second phantom acquired with the one or more cameras; and mapping a position of the one or more cameras to the first coordinate system.

In various embodiments of the aspect, the plurality of optical markers of the second phantom are arranged in a two-dimensional (2D) pattern, and the calibrating of the one or more cameras in the second coordinate system is achieved using images containing the optical markers arranged in the 2D pattern.

In various embodiments of the aspect, the second phantom further comprises one or more radiation markers, and in the defining of the position of the second phantom in the first coordinate system, the predetermined position of the second phantom relative to the first phantom can be verified using images containing the one or more radiation markers of the second phantom.

In various embodiments of the aspect, the calibrating of the one or more cameras comprises verifying intrinsic calibration of the one or more cameras using images containing the optical markers of the second phantom acquired with the one or more cameras.

In various embodiments of the aspect, the radiation machine comprises a source operable at a megavoltage (MV) energy level and an image detector operable to acquire the images containing the radiation markers of the first phantom with radiation from the source, and the method further comprises the step of determining an imaging isocenter between the source and the image detector using the images containing the radiation markers of the first phantom, and adjusting a position of the image detector if the imaging isocenter misaligns with the isocenter of the radiation machine.

In various embodiments of the aspect, the radiation machine comprises a source operable at a kilovoltage (KV) energy level and an image detector operable to acquire the images containing the radiation markers of the first phantom with radiation from the source, and the method further comprises the step of determining an imaging isocenter between the source and the image detector using the images containing the radiation markers of the first phantom, and adjusting a position of the image detector if the imaging isocenter misaligns with the isocenter of the radiation machine.

This Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a brief summary of certain forms the invention might take and are not intended to limit the scope of the invention. Other aspects and embodiments of the disclosure are described in the section of Detailed Description.

These and various other aspects, embodiments, features, and advantages of the disclosure will become better understood upon reading of the following detailed description in conjunction with the accompanying drawings.

DETAILED DESCRIPTION OF EMBODIMENTS

With reference to FIGS. 1-7, where like elements of similar structure or functions are represented by like numerals, various embodiments of a phantom device and a method of calibration and verification of an optical and/or radiation system will now be described. It should be noted that the figures are intended for illustration of embodiments but not for exhaustive description or limitation on the scope of the disclosure. Alternative structures and functional steps will be readily recognized as being viable without departing from the principle of the claimed invention.

Overview

In general, embodiments of the disclosure consolidate several phantoms into one solution, allowing calibration and verification of optical devices in a radiation coordinate system more effectively and efficiently. The combination of a radiation phantom with an optical markerboard allows both determination of the isocenter of a radiation machine and calibration and registration of optical devices in the radiation coordinate system with origin at the isocenter. The consolidated solution allows a fully automated procedure for identification of the isocenter of a radiation machine, calibration of an MV imaging system, a kV imaging system, and an optical system in the radiation coordinate system with minimal or no human interaction.

Figure 1:
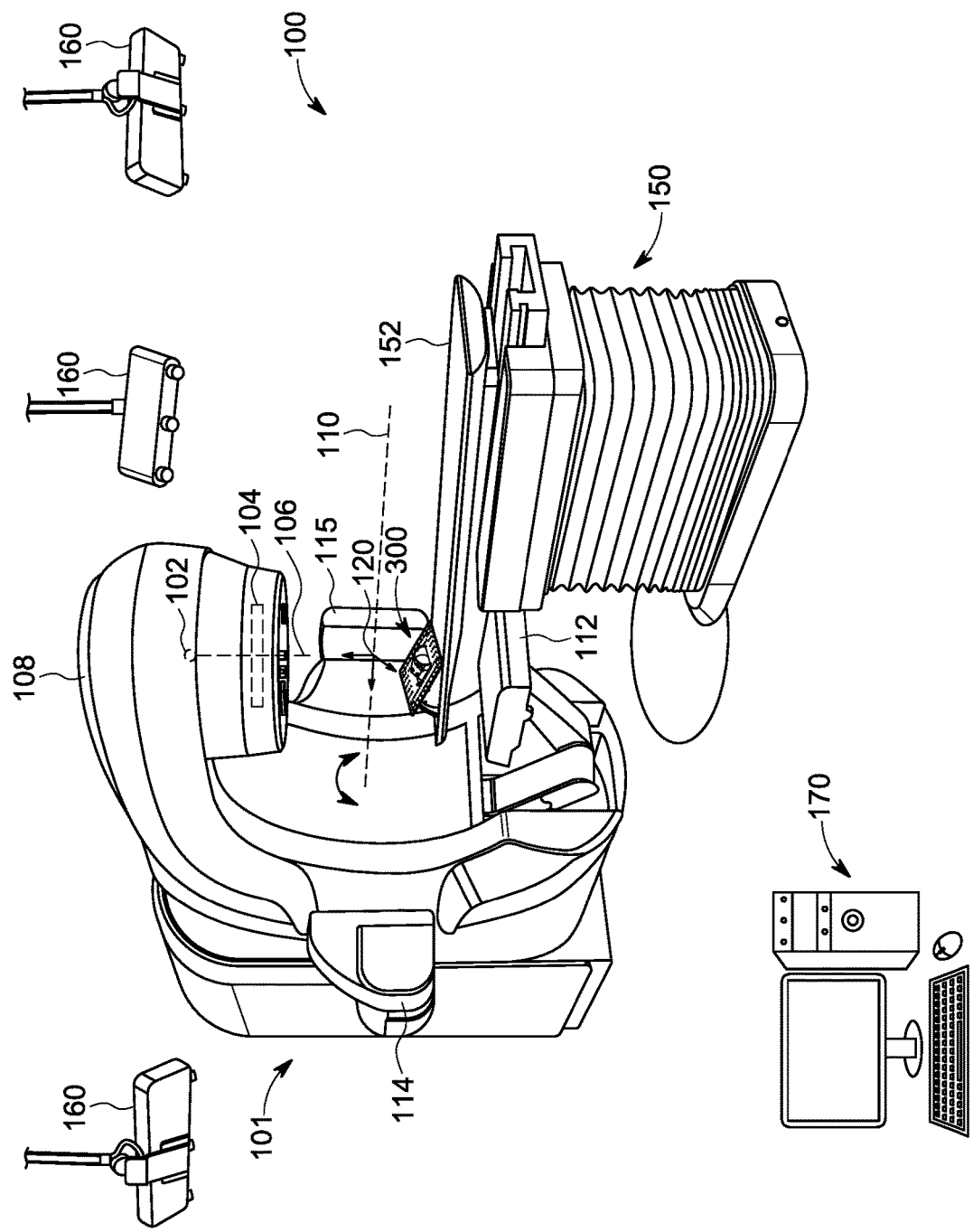
FIG. 1 is a simplified illustration of a radiation system according to embodiments of the disclosure.

FIG. 1 is a simplified illustration of a radiation treatment system 100 in which embodiments of the disclosure can be implemented. As illustrated, the system 100 includes a radiation machine 101, a couch 150, and one or more cameras 160. A computer system 170 connects with the radiation machine 101, the couch 150, and the one or more cameras 160, and controls their operations. In use, a patient (not shown) may be positioned on a couch top 152, which can move relative to the couch 150, or be moved by the couch 150 in multiple degrees of freedom, including translations and rotations in various directions, to align a treatment target in the patient to the isocenter 120 of the treatment machine 101. The one or more cameras 160 obtain images of the patient, the radiation machine 101, and/or the couch 150, and transmit the images to the computer system 170 for processing and viewing. The images can be used to aid patient setup, verify patient identification, monitor treatment, and/or provide treatment planning, etc. In some embodiments, the one or more cameras 160 may be a stereoscopic (3D) camera system operable to provide surface guided radiotherapy (SGRT). Stereoscopic cameras are known in the art and typically include a pair of cameras and a projector or structured light source. According to embodiments of the disclosure, a phantom device 300 can be positioned on the couch 150 or couch top 152 for calibration and/or verification of the one or more cameras 160 and/or the radiation machine 101. The phantom device 300 may be moved by the couch 150 and/or the couch top 152 in multiple degrees of freedom, including translations and rotations in various directions, to allow at least one of the one or more cameras 160 to view the entre or a portion of the phantom device 300, providing a large field of view (FOV) within at least the area in the range of motion of the couch or couch top.

With reference to FIG. 1, the radiation machine 101 may include a linear accelerator (not shown in FIG. 1) operable at a high energy level such as a megavoltage (MV) level to generate high energy electrons, and a source 102 such as a metallic target adapted to produce e.g., x-rays or other types of radiation suitable for therapeutic treatment (MV source). The radiation machine 101 may include various collimation devices to limit, define, or modify the characteristics of the radiation beam as it travels away from the source 102. The collimation devices may include a multileaf collimator (MLC) 104 operable to shape or dynamically shape the beam according to a treatment plan. The MLC 104 may be rotated about a central beamline 106, placing the MLC 104 in various orientations. The linear accelerator, source 102, various collimation devices including the MLC 104, and other devices or components, may be enclosed in a gantry 108, which can be in the form of a C-arm and rotate about a horizontal axis 110. Therefore, the radiation machine 101 can deliver radiation to a treatment target from various angles while the gantry 108 is stepped or swept around the patient according to a treatment plan. Any movement of the patient, the radiation machine 101, and the couch 150 can be monitored and/or guided by the one or more cameras 160.

The radiation machine 101 may include an electronic portal imaging device (EPID) 112 which, with the MV source 102, provides an MV imaging capability for the radiation machine 101. The MV imaging system 102, 112 may be used to aid patient setup, verify patient identification, and monitor treatment etc. The radiation machine 101 may also include an x-ray tube 114 operable at a kV energy level (kV source) and an image detector 115, providing a kV imaging capability for the radiation machine 101. The kV imaging system 114, 115 provides better contrast, resolution and other image qualities, and can be used to guide treatment and perform treatment planning, etc. The EPID 112, the kV source 114, and the image detector 115 may be supported by and rotated with the gantry 108.

Figure 2:
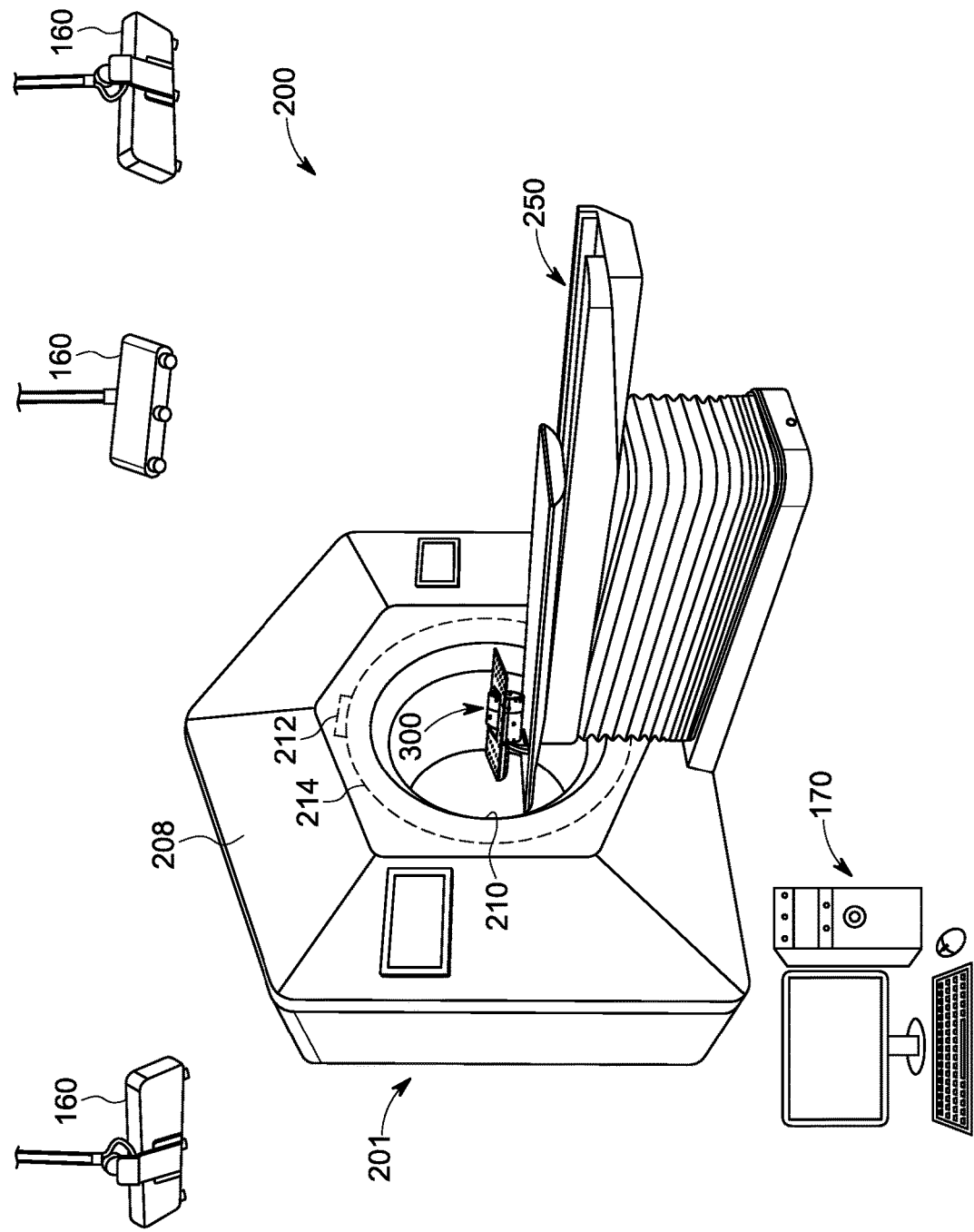
FIG. 2 is a simplified illustration of a radiation system according to embodiments of the disclosure.

It should be noted that while embodiments of the disclosure are described in conjunction with a radiation machine 101 having a gantry configuration in the form of a C-arm as illustrated in FIG. 1, the principle of the disclosure can be applied in a radiation machine having a gantry configuration in the form of an O-ring, or a robotic arm wherein the source of radiation and/or patient can be moved in multiple degrees of freedom. FIG. 2 shows a radiation treatment system 200 including a radiation machine 201 having a gantry configuration in the form of an O-ring. As illustrated, the system 200 includes a radiation machine 201, a couch 250, and one or more cameras 160. A computer system 170 connects with the radiation machine 201, the couch 250, and the one or more cameras 160, and controls their operations. The radiation machine 201 includes a housing 208, which defines an opening or a bore 210 allowing a patient or a portion of a patient on a couch to be positioned in the bore for receiving radiation. A linear accelerator (not shown), a source 212, an MLC (not shown), and other devices may be supported and rotated by or on a ring gantry 214 in the housing 208, allowing irradiation of a treatment target in the patient from multiple angles. The one or more cameras 160 obtain images of the patient, the radiation machine 201, and/or the couch 250, and transmit the images to the computer system 170 for processing and viewing. The images can be used to aid patient setup, verify patient identification, monitor treatment, provide treatment planning and/or treatment guidance.

It should be noted that while embodiments of the disclosure are described in conjunction with a treatment machine 101 or 201, the principle of the disclosure can be also applied in a diagnostic system such as a system of computed tomography (CT), cone beam computed tomography (CBCT), CT-simulation, MRI, and so on. Further, it will be appreciated that embodiments of the disclosure can be applied in various types of radiation systems, including systems producing radiation of x-rays, protons, heavy ions, electrons, and any other types of radiation.

With reference to FIG. 1, the radiation machine 101 has an isocenter or a radiation isocenter 120, a point or center of a small volume where radiation beams or axes of radiation beams intersect at all rotations of the source 102 during beam-on. Accurate positioning of a treatment target at the isocenter 120 allows delivery of radiation to the target while avoiding unnecessary irradiation of surrounding healthy organs or tissue. Therefore, determination or verification of the isocenter of a radiation machine is critical, especially in stereotactic radiosurgery (SRS) and stereotactic body radiation therapy (SBRT), where high dose of radiation is delivered to a treatment target of small size in a single or fewer fractions and less tolerance of errors allowed. Determination or verification of the radiation isocenter also allows calibration of an MV imaging system and a kV imaging system in the treatment coordinate system with origin at the isocenter.

Optical devices 160 such as stereoscopic (3D) cameras, 2D cameras, time-of-flight (ToF) cameras, LiDAR, or structured light cameras, etc., operating in various different wave lengths, are increasingly used in a radiation system for patient setup, patient identification, treatment monitoring, treatment planning and/or guidance, etc. The use of optical devices in a radiation system requires calibration of the optical devices in the radiation coordinate system. Conventionally, determination of the isocenter of a radiation machine, calibration and verification of optical devices, and registration of the optical devices in the radiation coordinate system are carried out separately using various different tools. Calibration of optical devices in a radiation coordinate system requires a multitude of calibration tools to perform various calibration steps. For instance, to calibrate stereoscopic cameras in a treatment or diagnostic coordinate system, conventional techniques use a calibration sheet to calibrate the stereo cameras, and a separate, x-ray detectable three-dimensional (3D) object to register the stereo cameras to the treatment or diagnostic coordinate system.

According to embodiments of the disclosure, a phantom device or universal phantom 300 is provided. The universal phantom 300, as shown in FIGS. 1-2, can be used to determine or verify the isocenter of a radiation machine, calibrate an MV imaging system and/or a kV imaging system equipped on the radiation machine, and perform other quality assurance. Furthermore, the universal phantom 300 can be used to calibrate optical devices and register the optical devices in the radiation coordinate system. The universal phantom 300 of the disclosure consolidates several phantoms into one solution, allowing determination of the isocenter of a radiation machine, calibration of a radiation imaging system, and calibration of an optical system in the radiation coordinate system more effectively and efficiently.

Universal Phantom

Figure 3A:
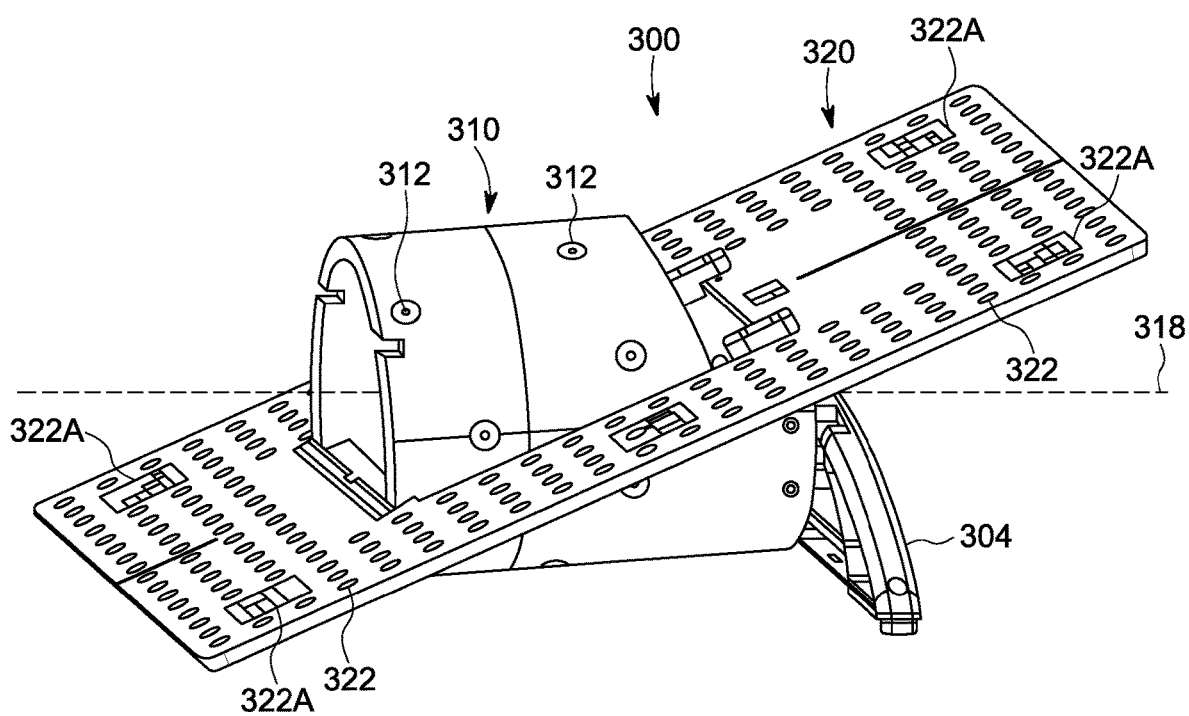
FIGS. 3A-3F depict an example phantom device according to embodiments of the disclosure.
Figure 3B:
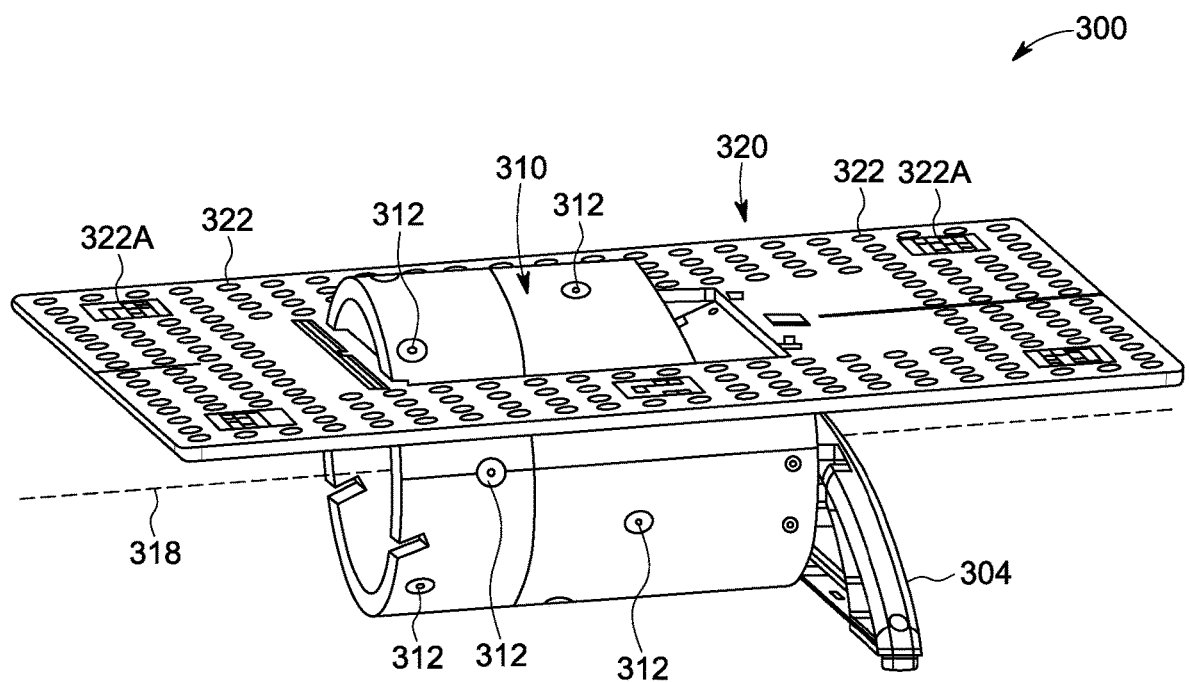

With reference to FIGS. 3A-3B, a universal phantom, or a phantom device, or an apparatus 300 according to embodiments of the disclosure is now described. As shown, the phantom device 300 includes a first phantom 310 and a second phantom 320. The first phantom 310 comprises a plurality of radiation markers 312. The second phantom 320 comprises a plurality of optical markers 322, 322A. The second phantom 320 is fixedly attachable to the first phantom 310 in a predetermined position, allowing a location and/or an orientation of the second phantom 320 to be fixed with respect to the first phantom 310 when in use.

As used herein, the term "phantom" broadly refers to an object, structure, or tool designed to evaluate, analyze, and/or tune the performance of various devices or systems, including x-ray, optical, MRI, or ultrasound devices or systems. As used herein, the term "radiation marker" refers to an object imageable by a radiation image detector when irradiated by or exposed to radiation. A radiation marker can be an object made of a metal such as tungsten, titanium, steel or other metal or metal alloy which can attenuate radiation to allow a radiation image detector to detect the effect of attenuation. A radiation marker as used herein may also refer to a radioactive substance or tracer as used in positron emission tomography (PET).

Figure 4:
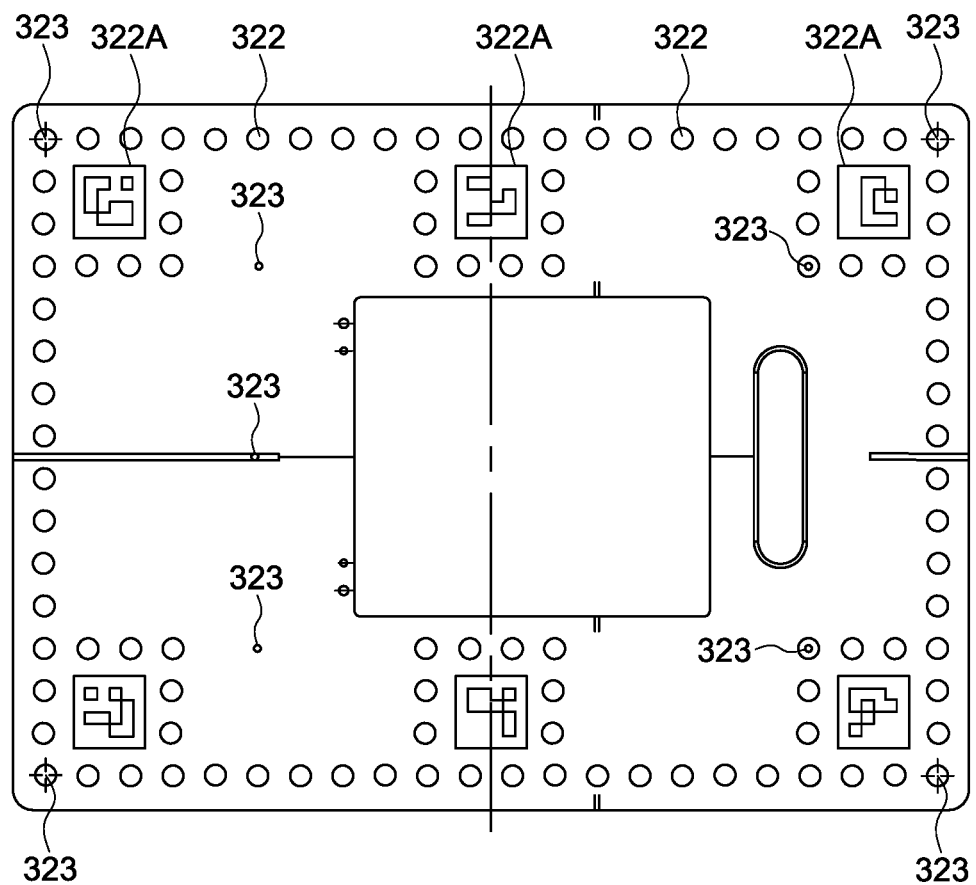
FIG. 4 depicts an example markerboard according to embodiments of the disclosure.
Figure 4A:
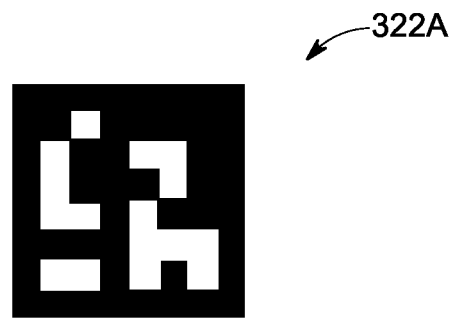
FIGS. 4A and 4B depict example optical markers.
Figure 4B:
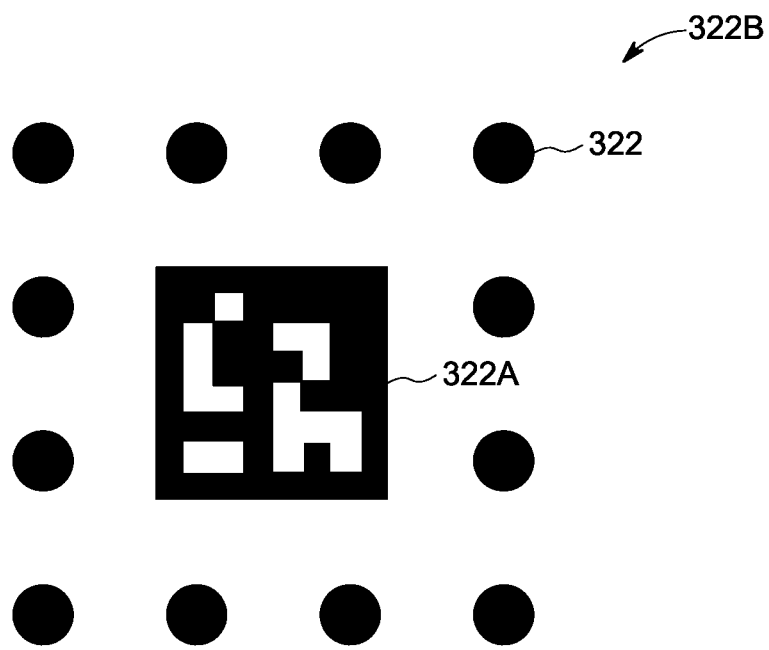

As used herein, the term "optical marker" refers to any marking, pattern, code, or any combination thereof imageable by an optical image detector. Example optical markers include markings arranged in a pattern such as circles or squares, chessboard, ArUco marker, QR-code, volumetric objects, active or passive reflectors, or any combination. FIG. 4 shows example optical markers including a combination of circular markers 322 and ArUco markers 322A arranged in a predetermined pattern according to embodiments of the disclosure. As shown in FIG. 4, the plurality of circular markers 322 (also referred to as "reference discs") may be grouped in a predetermined pattern (also referred to as "reference disc pattern"), dividing the markerboard into areas or regions e.g., six regions at the corners and sides of the markerboard. Each reference disc pattern may further include an ArUco marker 322A (six are shown) for denoting a particular reference disc pattern. FIG. 4A shows an example ArUco marker 322A. FIG. 4B shows an example reference disc pattern 322B including a number of circular markers 322 and an ArUco marker 322A. It should be pointed out that the optical markers 322, 322A and the pattern 322B of the optical markers 322 and 322A shown in FIGS. 4, 4A, and 4B are provided for illustration purposes. The principle of the disclosure is not limited by any particular types, number, and/or pattern of optical markers.

Figure 3C:
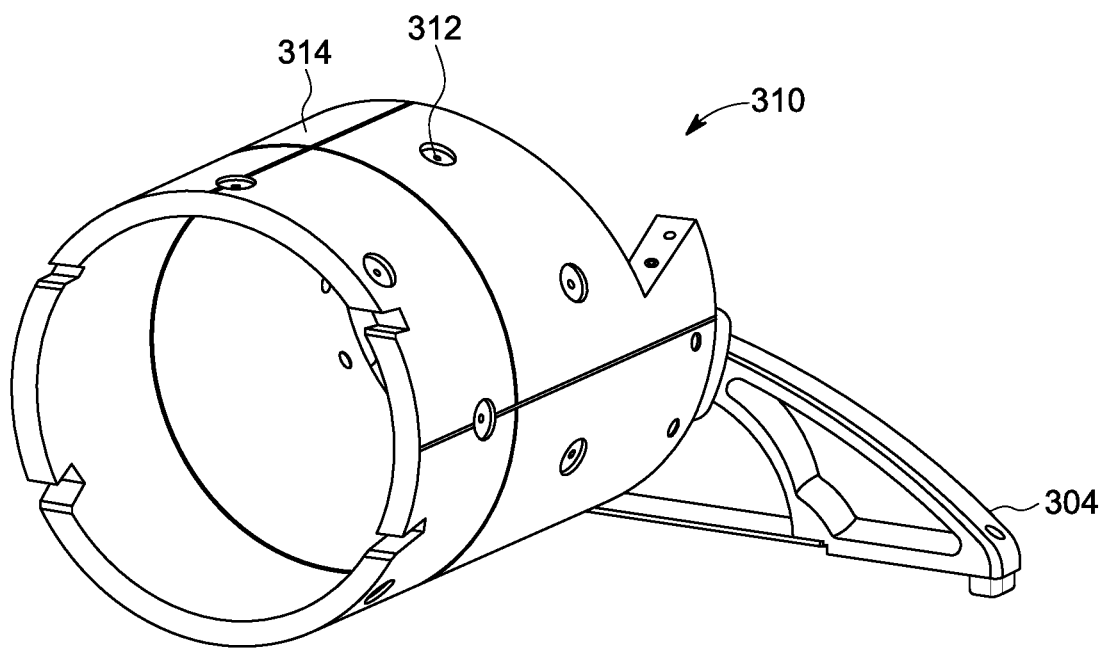
Figure 3D:
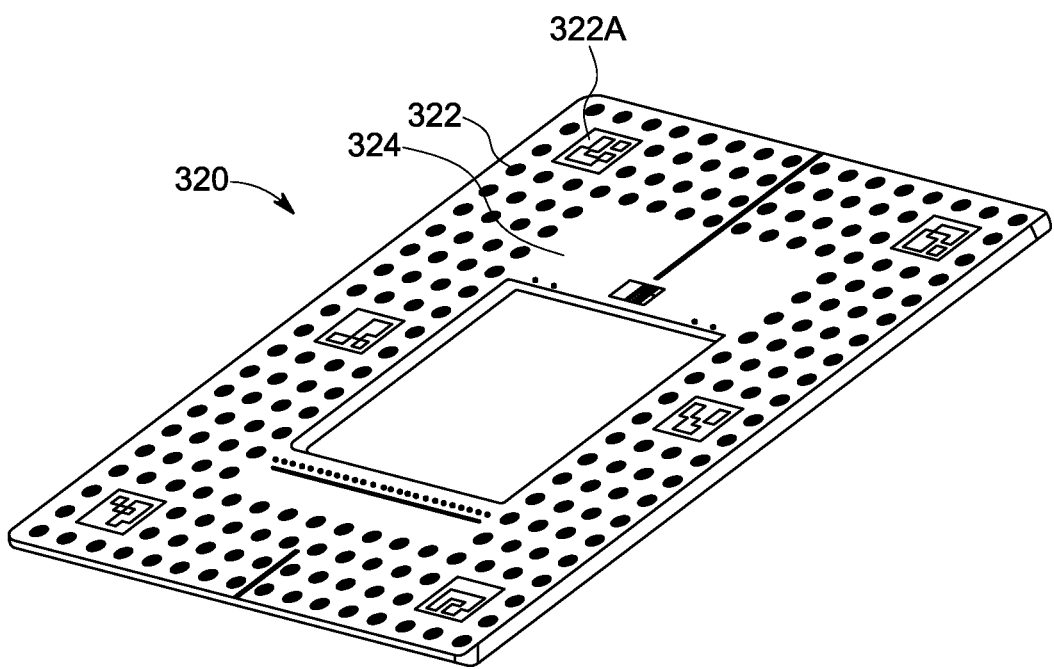

With reference to FIGS. 3C-3D, the first phantom 310 and the second phantom 320 can be in a modular form respectively, and assembled as a unit when in use. The modular design of the first phantom 310 and the second phantom 320 allows the location and/or orientation of the second phantom 320 relative to the first phantom 310 to be adjustable for use in different applications. FIG. 3A shows the second phantom 320 can be fixedly attached to the first phantom 310 in an orientation angled from the longitudinal axis 318 of the first phantom, suitable e.g., for use with a radiation machine 101 having a C-arm gantry as illustrated in FIG. 1. FIG. 3B shows the second phantom 320 can be fixedly attached to the first phantom 310 in an orientation generally parallel to the longitudinal axis 318 of the first phantom, suitable e.g., for use with a radiation machine 201 having an O-ring gantry as illustrated in FIG. 2.

With reference to FIGS. 3C-3D, the first phantom 310 may comprise a body 314 such as a three-dimensional (3D) body and a plurality of radiation markers 312 distributed in the 3D body. By way of example, the 3D body 314 may be in the form of a cylinder or a partial cylinder, a cube, a cuboid, or other regular or irregular forms. The 3D body 314 may be constructed from a radiation-transparent material such as polyoxymethylene or the like. The radiation markers 312 may be distributed or asymmetrically distributed in the 3D body 314, and precisely positioned in predetermined locations. Examples of the first phantom 310 include Drum Phantom and Cube Phantom available from Varian Medical Systems, Inc. of Palo Alto, CA.

With reference to FIGS. 3C-3D, the second phantom 320 may comprise a board member 324 and a plurality of optical markers 322, 322A arranged on or in the board member. The board member 324 may be in the form of a plate or a member having a planar surface allowing the optical markers 322, 322A to be arranged in a two-dimensional (2D) pattern. The board member 324 may be constructed from a radiation-transparent material such as polyoxymethylene or the like. Alternatively, the board member 324 is constructed from any other suitable materials. The optical markers 322, 322A can be in the form of circles, squares, chessboards, ArUco markers, QR-codes, or any combination thereof as described above. In the disclosure, the term "second phantom" may be used interchangeably with the term "markerboard." As an example, the second phantom 320 may include a plurality of ArUco markers 322A and a plurality of circular markers 322 arranged in a 2D pattern in the surface of the board member 324. FIG. 4 shows another example markerboard including a plurality of ArUco markers 322A and a plurality of circular markers 322 arranged in a 2D pattern.

In some embodiments, the second phantom 320 may comprise a plurality of radiation markers. The radiation markers can be distributed at predetermined locations in the board member 324, and used as references for verification of the location and/or orientation of the second phantom 320 relative to the first phantom 310 using radiation imaging. The radiation markers of the second phantom 320 can also be used to check the integrity of the markerboard 320 by determining the expected distances between the precisely positioned radiation markers. FIG. 4 shown nine radiation markers 323 distributed at the corners and in the middle portion of the markerboard for illustration purpose. It will be appreciated that more or fewer radiation markers can be included in the markerboard 320.

Figure 3E:
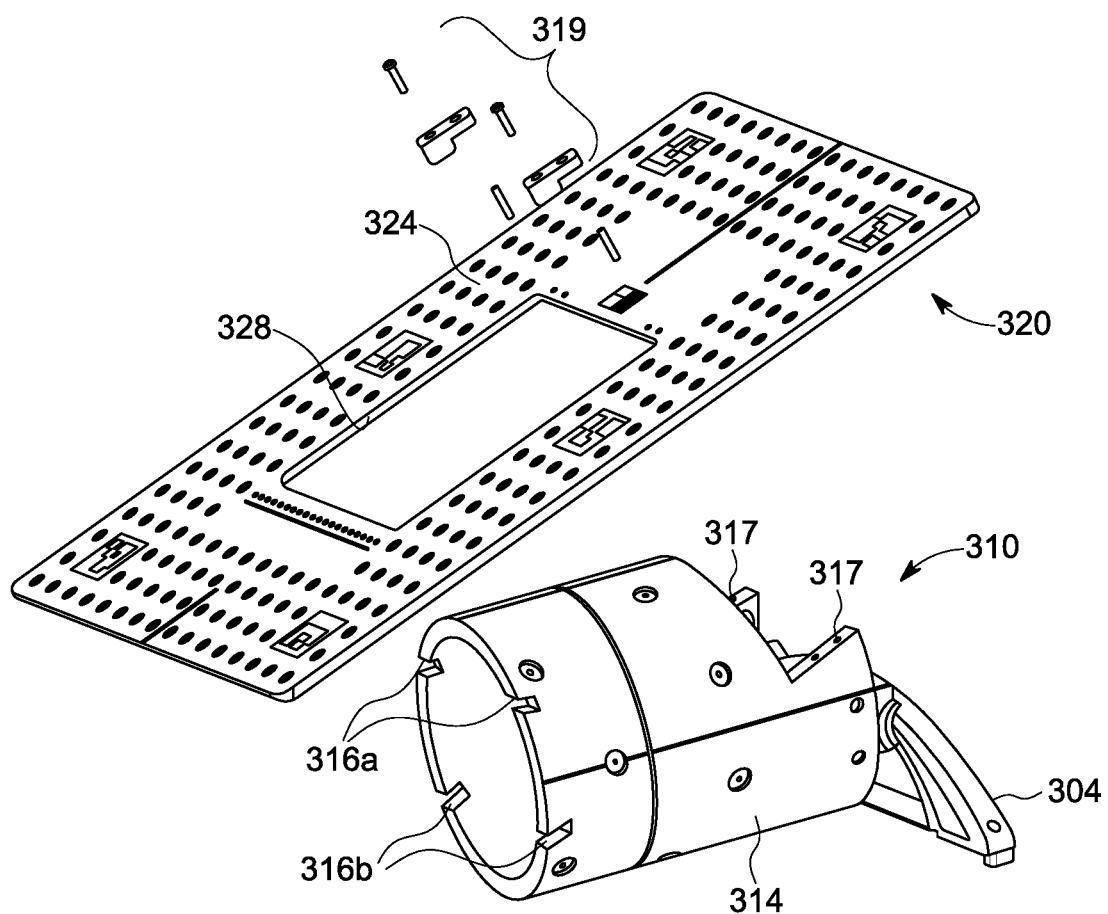
Figure 3F:
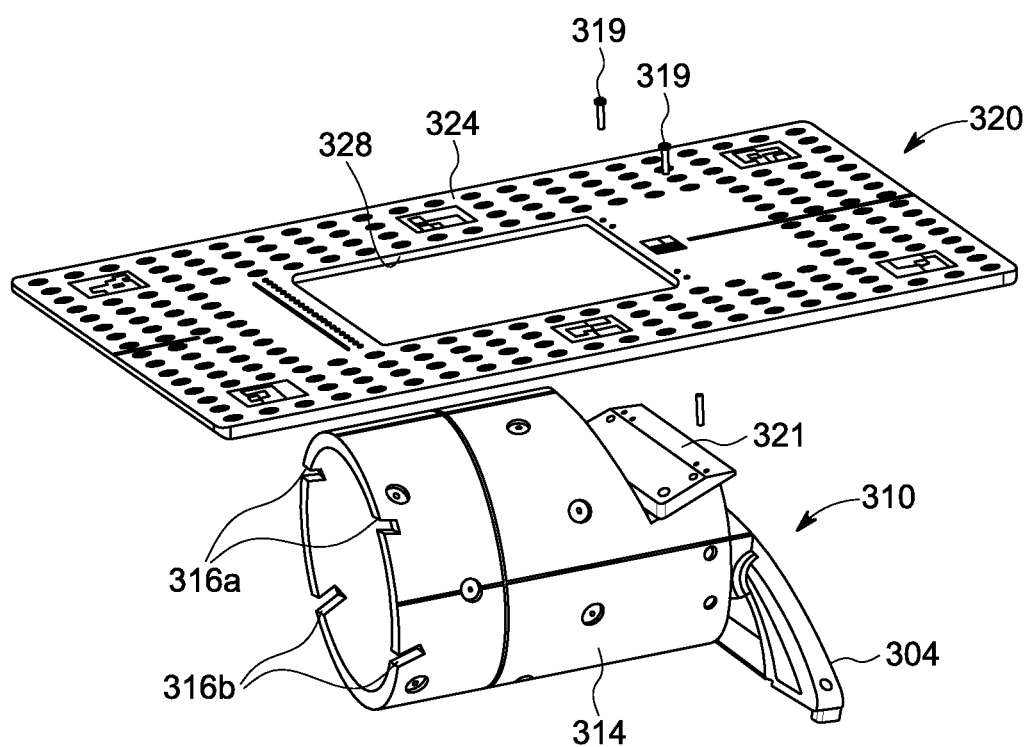

With reference to FIGS. 3E-3F, the second phantom 320 may be fixedly attached to the first phantom 310 by any suitable means. For instance, slots 316a, 316b may be provided at a side of the 3D body 314 of the first phantom 310, allowing the board member 324 of the second phantom 320 to be received in the slots. Apertures 317 may be provided in the 3D body 314, allowing the board member 324 of the second phantom 320 to be secured to the 3D body 314 of the first phantom 310 by suitable fasteners such as screws, nuts, pins, clips, latches or the like 319.

In the specific embodiments shown in FIG. 3E-3F, slots 316a, 316b are provided adjacent to both an upper side and a lower side in one end of the 3D body 314 of the first phantom 310. Slots 316b adjacent to the lower side of the 3D body 314 of the first phantom 310 can be configured to allow the board member 324 of the second phantom 320 to be positioned in an orientation angled from the longitudinal axis 318 of the 3D body 314, as shown in FIG. 3E. Fasteners such as screws, nuts, pins, clips, or the like 319 can be used to secure the board member 324 of the second phantom 320 to the 3D body 314 of the first phantom. Slots 316a adjacent to the upper side of the 3D body 314 of the first phantom 310 can be configured to allow the board member 324 of the second phantom 320 to be positioned in an orientation generally parallel to the longitudinal axis 318 of the 3D body 314, as shown in FIG. 3F. Fasteners such as screws, nuts, or the like 319 and an interface plate 321 can be used to secure the board member 324 of the second phantom 320 to the 3D body 314 of the first phantom 314.

With reference to FIGS. 3E-3F, in specific embodiments, the board member 324 of the second phantom 320 may have a cutout 328 e.g., in a middle portion of the board member 324, allowing the 3D body 314 or a portion of the 3D body 314 of the first phantom 310 to be disposed therewithin. The cutout 328 in the board member 324 allows the second phantom 320 to be fixedly attached to the first phantom 310 in a relatively compact manner.

The fixed attachment of the second phantom 320 to the first phantom 310 allows the location and/or orientation of the second phantom 320 relative to the first phantom 310 to be predetermined or known. Because the isocenter of a radiation system can be determined or verified using the first phantom 310, and as a result the location and/or orientation of the first phantom 310 can be defined in the radiation coordinate system with origin at the isocenter, the location and/or orientation of the second phantom 320 in the radiation coordinate system can also be determined based on the known relationship between the second phantom 320 and the first phantom 310. The one or more cameras 160, which can be calibrated or verified using the second phantom 320, can be then mapped or registered into the radiation coordinate system with origin at the isocenter.

With reference to FIGS. 3A-3F, the phantom device 300 may comprise a frame or interface plate 304 for attachment of the phantom device 300 to a couch or couch top. The interface plate 304 may have suitable features for attaching to a side of the 3D body 314 of the first phantom 310 and to a couch or couch top. In some embodiments, the phantom device 300 may include a micrometer moving mechanism (not shown), allowing the position of the phantom device 300 to be accurately adjusted.

Calibration Method

Figure 5:
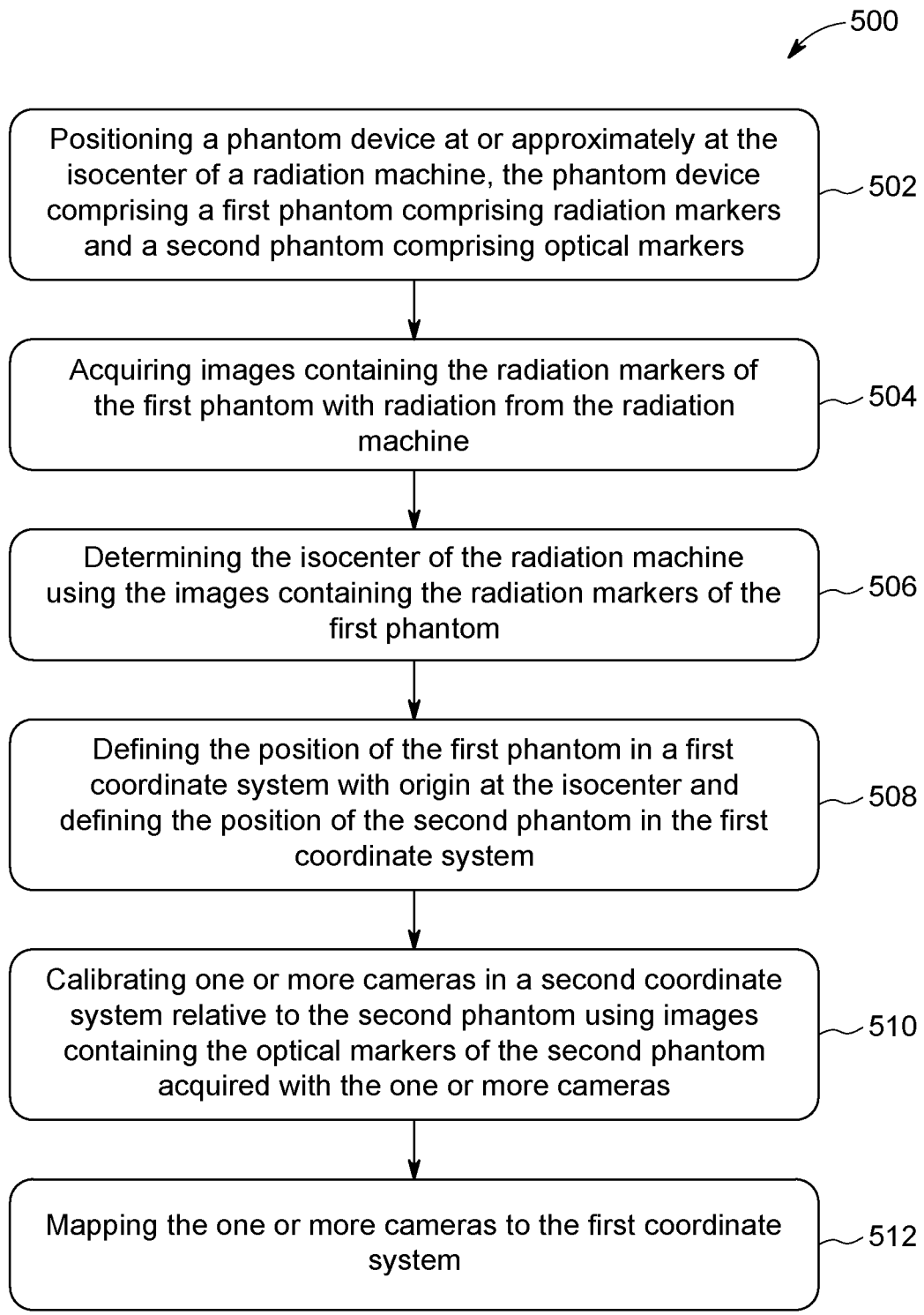
FIG. 5 is a flowchart illustrating an example method according to embodiments of the disclosure.

With reference to FIG. 5, a calibration method 500 is now described. In general, the method employs a phantom device to consolidate the tasks of determining the isocenter of a radiation machine, calibrating optical devices, and registering the optical devices in a radiation coordinate system with origin at the isocenter, thereby allowing calibration of optical devices in a radiation coordinate system effectively and efficiently. The method 500 can be carried out in a radiation system 100, 200 as illustrated in FIGS. 1-2, or any other suitable treatment, diagnostic, simulation, and research and development system. A suitable radiation system includes a radiation machine, a couch or supporting device, one or more optical devices or cameras, and a computer system connecting with the radiation machine, the couch, and the one or more cameras. The radiation machine includes a gantry and a source of radiation supported by the gantry. The gantry or the source of radiation is rotatable about a rotation axis.

With reference to FIG. 5, the method 500 may begin at step 502 where a phantom device is positioned at or approximately at the isocenter of the radiation machine. The phantom device may be mounted on the couch or couch top which is movable in multiple degrees of freedom. The phantom device can be roughly aligned to the isocenter of the radiation machine by a clinical staff with an orientation aid such as in-room lasers. The phantom device may comprise a first phantom comprising a plurality of radiation markers and a second phantom comprising a plurality of optical markers. The second phantom optionally comprises a plurality of radiation markers. The second phantom is fixedly attached to the first phantom in a predetermined position. The phantom device may be the same as or similar to the universal phantom 300 described in conjunction with FIGS. 3A-3F. As an example, the first phantom may comprise a 3D body (e.g., hollow-cylinder) with multiple (e.g., 16) metallic balls or ball bears (BBs) asymmetrically distributed in the 3D body. The second phantom may comprise a board member having a planar surface and a plurality of optical markers arranged in a 2D pattern. A plurality of radiation markers may also be included in the second phantom.

At step 504, the method proceeds to acquire images containing the radiation markers of the first phantom with radiation from the radiation machine. The images containing the radiation markers of the first phantom may be acquired using an MV imaging system and/or a kV imaging system of the radiation machine. For instance, in a treatment room, images of the first phantom can be acquired with an MV imaging system of a treatment machine equipped with an EPID. Alternatively, or additionally, images of the first phantom may be acquired with a kV imaging system including a kV source and an image detector equipped on the treatment machine. Multiple images of the first phantom can be taken at different gantry angles or source angles between 0 and 360 degrees. In cases where MLC rotations are involved, an additional plate including a radiation marker such as a metallic pin may be inserted in an accessory slot in the gantry head. The MLC may be rotated to multiple orientation angles, and at each of the orientation angles, multiple MV images and/or kV images of the first phantom can be acquired at different gantry angles or source angles between 0 and 360 degrees.

At step 506, the method proceeds to determine or verify the radiation isocenter or the isocenter of the radiation machine using the images of the first phantom acquired with radiation from the radiation machine. Determining or verifying the isocenter of a radiation machine using radiation images of a phantom is generally known. Winston-Lutz (WL) method is one of the known methods. IsoCal™ is another known method developed by and available from Varian Medical System, Inc. of Palo Alto, CA. The WL and IsoCal™ methods are incorporated herein by reference. Briefly and generally, in an IsoCal™ procedure, the MV images and/or kV images are analyzed to identify the locations of the radiation markers of the phantom and/or the metallic pin of the MLC plate in the images. A geometric analysis is performed using the identified locations of the radiation markers to calculate the intersection of axes of the radiation beam from multiple gantry angles, or the radiation isocenter of the radiation machine. U.S. Pat. No. 7,844,094 issued on Nov. 30, 2010 describes a method of determining a geometric parameter of a radiation machine using radiation images of a phantom, the disclosure of which is incorporated herein by reference.

In accordance with embodiments of the disclosure, the MV images and/or kV images are analyzed, and geometric analysis performed to calculate the imaging isocenter of the MV imaging system and/or kV imaging system. This allows determination of any misalignment between the MV image detector and the MV source, and/or between the kV image detector and the kV source, and allows correction or adjustment of the position of the MV image detector and/or kV image detector as a function of the gantry angle, thereby allowing alignment of the imaging isocenter of the MV imaging system and/kV imaging system with the radiation isocenter of the treatment machine.

In alternative embodiments where the method is implemented in a diagnostic system such as a CT machine or CT-simulator, the method may proceed at steps 504 and 506 to acquire images of the first phantom in a CT-room with a CT machine or CT-simulator, and determine or verify the isocenter of the CT machine or CT-simulator using the CT images. As such, the CT images can be obtained and frame of reference (FOR) stored as a structure set e.g., in DICOM file format. Optical markers in the second phantom can be used to relate the position of the second phantom relative to the frame of reference using the reference CT from the CT room.

Figure 6:
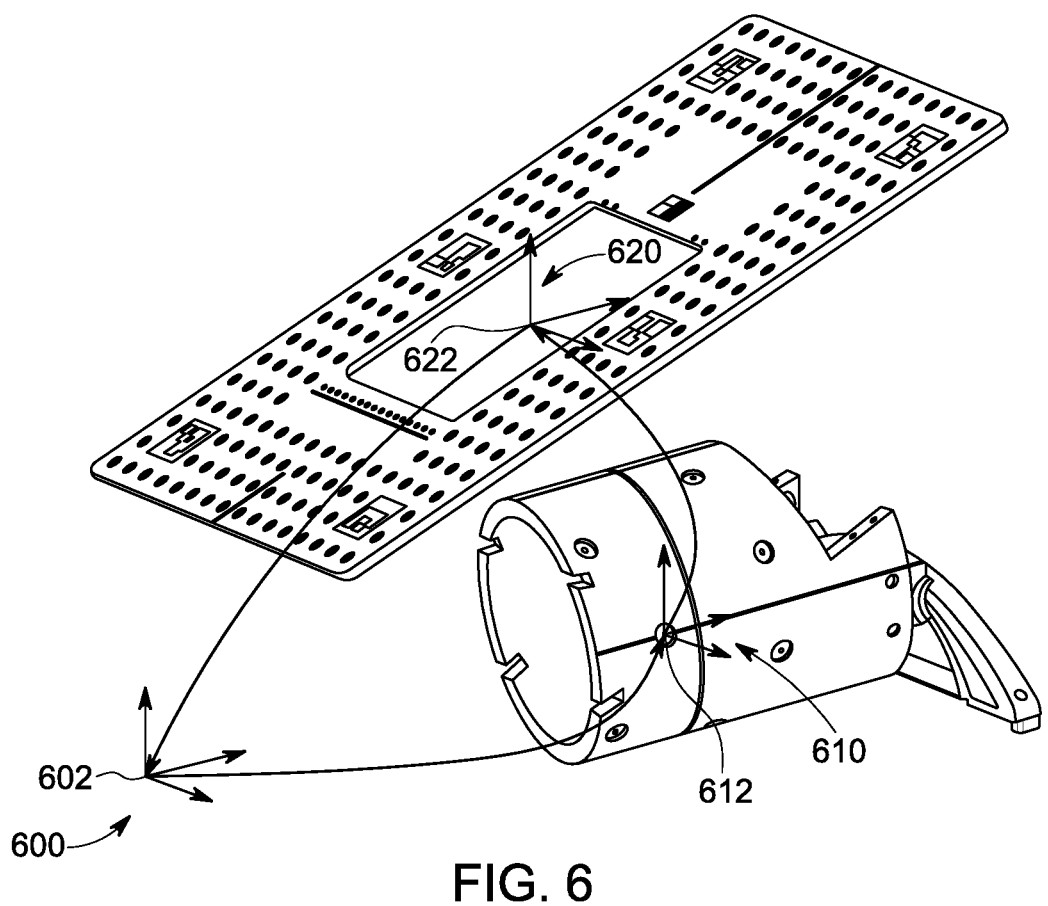
FIG. 6 illustrates coordinate systems in connection with a phantom device in a radiation system according to embodiments of the disclosure.

At step 508, the method proceeds to define or determine the position of the first phantom in a first coordinate system or a radiation coordinate system with origin at the isocenter, and define or determine the position of the second phantom in the radiation coordinate system. For illustration, FIG. 6 shows a first coordinate system or a radiation coordinate system 600 with origin 602 at the isocenter of the radiation machine, and a second coordinate system or a common optical coordinate system 620 with origin 622 with respect to the second phantom or markerboard for calibration of the one or more optical devices. The location of the center 612 of the radiation marker pattern of the first phantom and a coordinate system 610 with origin at the center 612 are also shown. It should be noted that the separation distance among the origins 602, 612, and 622 of the coordinate systems 600, 610, and 620 is exaggerated for clarity of illustration. For the phantom device comprising a first phantom and a second phantom used in the method is positioned at or approximately at the isocenter of the radiation machine, the origins 602, 612, 622 of the coordinate systems 600, 610 and 620 may coincide or approximately coincide. The origin 622 of the common optical coordinate system 620 is preferably set at or close to the radiation isocenter 602 such that the one or more cameras can readily view the optical markers of the second phantom. As described above, the isocenter 602 of the radiation machine can be determined or verified by using radiation images of the first phantom, and as a result, the location of the center 612 and the orientation of the the first phantom can be defined or determined in the radiation coordinate system 600. Because the second phantom is fixedly attached to the first phantom in a predetermined relationship, the location and orientation of the second phantom can also be defined or determined in the radiation coordinate system 600. In alternative embodiments, the second phantom may additionally comprise a plurality of radiation markers, and the location and orientation of the second phantom relative to the first phantom can be verified using radiation images containing the radiation markers in the second phantom. In defining the position of the second phantom in the radiation coordinate system 600, Step 508 may provide a first transformation matrix to transform the position, or the location and orientation of the first phantom into the radiation coordinate system, and a second transformation matrix to establish the relation between the position of the second phantom and the position of the first phantom.

With reference to FIG. 5, at step 510, the method proceeds to calibrate the one or more cameras in a second coordinate system relative to the second phantom (optical coordinate system 620 in FIG. 6), using images containing the optical markers acquired with the one or more cameras. By way of example, the one or more cameras may be 3D cameras, and images containing the optical markers of the second phantom are obtained with the 3D cameras or with cameras within the 3D cameras. Using the 2D patterns of the optical markers arranged on the markerboard, the 3D cameras can be aligned to each other, and scales be adjusted to a second coordinate system or an optical coordinate system relative to the markerboard common for each of the one or more 3D cameras. The relative positions of the 3D cameras in the second coordinate system can be expressed by a separate or third transformation matrix. Calibration of cameras or 3D cameras using optical markers is generally known and various methods have been developed. Therefore, detailed description of steps of calibration is omitted herein to focus on description of embodiments of the disclosure.

In some embodiments, at step 510 the method may optionally proceed to verify the intrinsic parameters of factory-calibrated cameras. For instance, the one or more cameras may be structured light 3D cameras, which may include a pair of cameras and a light projector. Factory calibration is typically conducted to align the two cameras to each other and the projector, and calculate out distortions and scale errors ("intrinsic calibration"). The second phantom comprising a board member and optical markers arranged in a 2D pattern can be used to verify the intrinsic calibration by assessing the brightness and pattern contrast, quality of epi-polar lines, and scale of an individual camera before merging them, by describing the relation of the camera by a matrix structure. Slight adjustment of calibration files is possible if deviations do not require a mechanical adjustment.

At step 512, the method proceeds to register or map the position of the one or more cameras into the first coordinate system. Using the transformation matrices from Step 508 and the transformation matrix from Step 510, any point in the common optical coordinate system can be mapped into the radiation coordinate system with origin at the isocenter.

It should be pointed out that in illustrating various functional steps of a calibration method in connection with FIG. 5, no particular order is implied by the arrangement of blocks shown and described. Further, it will be appreciated that more or fewer steps, actions, or processes may be incorporated into the method without departing from the scope of the disclosure. For instance, the method can be implemented in a radiation system without an optical system, and the universal phantom of the disclosure can still be used to calibrate and verify the radiation machine. In another example, the method can be implemented for calibration of other types of cameras such as ToF, Lidar, Structured Light Cameras generally used for patient setup or rough positioning on the couch, and the universal phantoms of the disclosure can still be used for calibration of these types of cameras. In some embodiments, the universal phantom of the disclosure can also be used to calibrate 2D cameras for patient identification, eliminating the need for extra phantom or special bar on the couch top for registering the 2D cameras as in conventional patient identification techniques.

Advantageously, the use of a universal phantom according to embodiments of the disclosure consolidates the tasks of calibration and registration of optical devices in a radiation coordinate system. Conventional methods use separate calibration tools respectively for calibration and registration of cameras in a radiation coordinate system, e.g., a calibration sheet for calibration and a separate calibration cube for registration to a radiation treatment system. In registration to the radiation treatment system, a 3D computer model of a reference surface of a physical calibration cube is used, and surface matching and modeling of the physical calibration cube are performed. According to embodiments of the disclosure, calibration of 3D cameras can be performed using optical markers arranged in a 2D pattern on a markerboard, and registration of the markerboard to a radiation coordinate system can be achieved based on a priori knowledge or by using radiation imaging.

The method of the disclosure described in conjunction with FIG. 5 may be embodied in a computer system according to embodiments of the disclosure. The invention may be in the form of a computer product comprising a computer-readable medium storing or carrying instructions which, when executed by a computer processor, cause the computer processor to perform the methods described in the disclosure. The instructions may be implemented as software code to be executed by a processor using any suitable computer language such as, Java, C++, C#, Perl, Python or other computer languages and techniques. The computer-readable medium may include any suitable medium that is capable of storing or encoding a sequence of instructions for execution by the computer processor and that causes the computer processor to perform any one of the methodologies of the present invention. The computer-readable medium shall accordingly include, but not be limited to, solid-state memories, optical and magnetic disks. Examples of computer-readable medium include volatile and nonvolatile, removable and non-removable media for storage of computer-readable instructions. By way of non-limiting example, the computer-readable medium includes random access memory (RAM), read only memory (ROM), electrically erasable programmable ROM (EEPROM) flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information. In some embodiments, the instructions or software program may be encoded and transmitted using carrier signals adapted for transmission via wired, optical, and/or wireless networks conforming to a variety of protocols, including the Internet. As such, a computer-readable medium may be created using a data signal encoded with such programs. A computer-readable medium encoded with the program code may be packaged with a compatible device or provided separately from other devices e.g., via Internet download. Further, any such computer-readable medium may reside on or within a computer product e.g., a hard drive, a CD, or an entire computer system.

Figure 7:
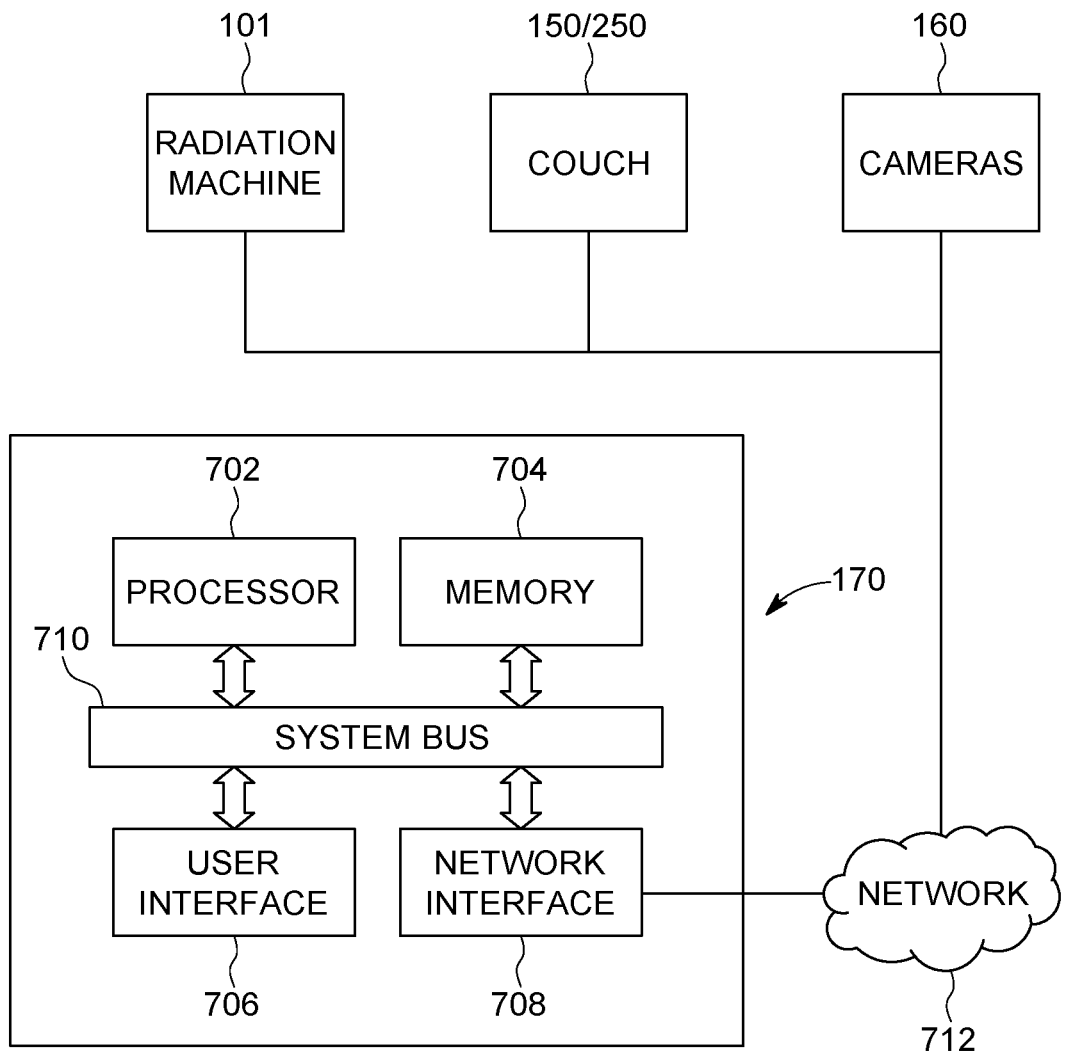
FIG. 7 is a diagram illustrating a computing system.

With reference to FIG. 7, the computer system 170 shown in FIGS. 1-2 may generally comprise a processor 702, memory 704, a user interface 706, and a network interface 708, each of which is coupled to a system bus 710.

The processor 702 may include a central processing unit (CPU) that is generally known in the art, such as an INTEL® processor or an AMD® processor, or a graphical processing unit (GPU), such as an NVIDIA® GPU, or other type of processing unit. The processor 702 may retrieve and execute computer-executable instructions from the memory 704, which may cause the processor 702 to perform any of the methods and/or steps according to the embodiments of this disclosure described above.

The memory 704 may include any one of or a combination of volatile memory elements and nonvolatile memory elements. The memory 704 may include a random-access memory (RAM) or other dynamic storage device for storing information and instructions to be executed by the processor 702, and for storing temporary variables or other intermediate information during execution of instructions by the processor 702. The memory 704 may also include read-only memory (ROM) or other static storage device for storing static information and instructions for the processor 702. The memory 704 may further include a data storage device such as a magnetic disk or optical disk, for storing information and instructions. The memory 704 (e.g., a non-transitory computer-readable medium) may comprise programs (logic) for operating the computer system and for performing applications including calculation of a radiation and/or optical system as described above, or other treatment planning applications. In addition, the memory 704 may include a database storing any information that can be selected by a user, such as a radiation oncologist or radiation therapist.

The user interface device 706 may include components with which a user interacts with the computer system 170, such as a keyboard, pointing device, pen, touch input device, voice input device, or the like. Output devices such as a display device, printer, speaker etc. may also be included in the computer system 170.

The network interface 708 allows the computer system 170 to communicate with the radiation machine 101/201, couch 150/251, cameras 160, and other devices or systems over a communication network 712 such as the Internet or an intranet (e.g., a local area network). The network interface 708 may include a Wi-Fi interface, Ethernet interface, Bluetooth interface, or other wireless or wired interfaces. The network interface 708 allows the computer system 170 to receive and send electrical, electromagnetic, and/or optical signals that carry data streams representing various types of information.

Various embodiments of a universal phantom and a method of calibration of optical devices in a radiation coordinate system have been described with reference to figures. It should be noted that the figures are intended to facilitate illustration and some figures are not necessarily drawn to scale. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. Further, the term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise. The term "coupled," "supported," "connected," "mounted", and variations are used broadly and encompass both direct and indirect couplings, supports, connections, and mounting.

Those skilled in the art will appreciate that various other modifications may be made. All these or other variations and modifications are contemplated by the inventors and within the scope of the invention.

What is claimed is:

1. An apparatus, comprising:
 a first phantom including a plurality of radiation markers; and
 a second phantom including a plurality of optical markers, the second phantom being fixedly attachable to the first phantom in a position, the plurality of optical markers including a first optical marker and a second optical marker, and the first phantom being between the first optical marker and the second optical marker.

2. The apparatus of claim 1, wherein the first phantom comprises a three-dimensional (3D) body, and the plurality of radiation markers are distributed in the 3D body.

3. The apparatus of claim 1, wherein the second phantom comprises a board member having a planar surface, and the plurality of optical markers are in a two-dimensional (2D) pattern on the planar surface.

4. The apparatus of claim 3, wherein the second phantom further comprises a plurality of radiation markers.

5. The apparatus of claim 3, wherein a portion of the board member of the second phantom is radiation-transparent.

6. The apparatus of claim 1, wherein
the second phantom comprises a modular unit; and
the second phantom is fixedly attachable to the first phantom, via the modular unit, in a first orientation and a second orientation, the second orientation being different from the first orientation.

7. The apparatus of claim 1, wherein
the first phantom comprises a three-dimensional (3D) body, the plurality of radiation markers being distributed in the 3D body;
the second phantom comprises a board member having a planar surface, the plurality of optical markers being in a two-dimensional (2D) pattern on the planar surface; and
the second phantom is fixedly attachable to the 3D body of the first phantom, via the board member, in a first orientation and a second orientation, the second orientation being different from the first orientation.

8. The apparatus of claim 7, wherein
a shape of the 3D body of the first phantom is at least one of a cylinder, a partial cylinder, or a cube;
the board member of the second phantom has a cut-out; and
a portion of the 3D body of the first phantom is in the cut-out of the board member.

9. The apparatus of claim 8, wherein the second phantom further comprises a plurality of radiation markers.

10. The apparatus of claim 1, further comprising:
a radiation machine comprising a source operable to produce radiation, the radiation including at least one of x-rays, protons, heavy ions, or electrons.

11. The apparatus of claim 10, further comprising:
one or more optical devices.

12. The apparatus of claim 11, further comprising:
a positioning device configured to
support the first phantom and the second phantom, and
move relative to the source such that a view of at least one of the one or more optical devices includes at least a portion of the first phantom or the second phantom.

13. The apparatus of claim 10, wherein the radiation machine is configured to operate at a megavoltage energy level, and the source is configured to produce radiation for at least one of treatment or imaging.

14. The apparatus of claim 10, wherein the radiation machine is operable at a kilovoltage energy level, and the source is configured to produce radiation for at least one of imaging or treatment.

15. A method of calibrating a system, the system including a radiation machine and one or more cameras, and the method comprising:
positioning a phantom device at an approximate isocenter of the radiation machine, the phantom device including a first phantom and a second phantom, the first phantom including a plurality of radiation markers, the second phantom including a plurality of optical markers, and the second phantom being fixedly attachable to the first phantom;
acquiring first images containing the plurality of radiation markers of the first phantom using radiation from the radiation machine;
determining a verified isocenter of the radiation machine using the first images;
defining a position of the first phantom in a first coordinate system, the first coordinate system having an origin at the verified isocenter;
defining a position of the second phantom in the first coordinate system based on a position of the second phantom relative to the first phantom;
calibrating the one or more cameras in a second coordinate system relative to the second phantom using second images containing the plurality of optical markers acquired with the one or more cameras; and
mapping a position of the one or more cameras to the first coordinate system.

16. The method of claim 15, wherein the plurality of optical markers are in a two-dimensional (2D) pattern, and the second images contain the plurality of optical markers in the 2D pattern.

17. The method of claim 16, wherein
the second phantom further comprises a plurality of radiation markers; and
the defining of the position of the second phantom in the first coordinate system includes verifying the position of the second phantom relative to the first phantom using the first images, the first images containing the plurality of radiation markers of the second phantom.

18. The method of claim 16, wherein the calibrating of the one or more cameras comprises verifying intrinsic parameters of the one or more cameras using the second images.

19. The method of claim 15, wherein
the radiation machine includes
a source operable at a megavoltage (MV) energy level, and
an image detector operable to acquire the first images using radiation from the source; and
the method further comprises:
determining an imaging isocenter between the source and the image detector using the first images, and
adjusting a position of the image detector in response to determining that the imaging isocenter is misaligned with the verified isocenter.

20. The method of claim 15, wherein
the radiation machine includes
a source operable at a kilovoltage (kV) energy level, and
an image detector operable to acquire the first images using radiation from the source; and
the method further comprises:
determining an imaging isocenter between the source and the image detector using the first images, and
adjusting a position of the image detector in response to determining that the imaging isocenter is misaligned with the verified isocenter.

21. A non-transitory computer-readable medium storing executable instructions for calibrating a system, the system including a radiation machine and one or more cameras, the instructions, when executed by one or more processors, configuring the one or more processors to cause the system to:

position a phantom device at an approximate isocenter of the radiation machine, the phantom device including a first phantom and a second phantom, the first phantom including a plurality of radiation markers, the second phantom including a plurality of optical markers, and the second phantom being fixedly attached to the first phantom;

acquire first images containing the plurality of radiation markers of the first phantom using radiation from the radiation machine;

determining a verified isocenter of the radiation machine using the first images;

determine a position of the first phantom in a first coordinate system, the first coordinate system having an origin at the verified isocenter; and define a position of the second phantom in the first coordinate system based on a position of the second phantom relative to the first phantom;

calibrate the one or more cameras in a second coordinate system relative to the second phantom using second images containing the plurality of optical markers acquired with the one or more cameras; and map a position of the one or more cameras to the first coordinate system.

* * * * *